US009550705B2

(12) United States Patent
Tosin et al.

(10) Patent No.: US 9,550,705 B2
(45) Date of Patent: *Jan. 24, 2017

(54) OLEFIN OLIGOMERIZATION PROCESS

(75) Inventors: Geraldine Tosin, Notre Dame de Gravenchon (FR); An Verberckmoes, Serskamp (BE); Helge Jaensch, Brussels (BE); Georges M. K. Mathys, Bierbeek (BE); Machteld M. Mertens, Flemington, NJ (US); Sourav Saha, Fremont, CA (US); Hailian Li, Union City, CA (US); Robert James Saxton, San Rafael, CA (US)

(73) Assignee: ExxonMobill Chemical Patents Inc., Baytown, TX (US)

( * ) Notice: Subject to any disclaimer, the term of this patent is extended or adjusted under 35 U.S.C. 154(b) by 262 days.

This patent is subject to a terminal disclaimer.

(21) Appl. No.: 14/233,199

(22) PCT Filed: Jun. 14, 2012

(86) PCT No.: PCT/EP2012/061366
§ 371 (c)(1),
(2), (4) Date: Apr. 7, 2014

(87) PCT Pub. No.: WO2013/013886
PCT Pub. Date: Jan. 31, 2013

(65) Prior Publication Data
US 2014/0221716 A1  Aug. 7, 2014

(30) Foreign Application Priority Data

Jul. 25, 2011 (EP) .................................... 11175235

(51) Int. Cl.

| | | |
|---|---|---|
| *C07C 2/10* | (2006.01) | |
| *B01J 20/08* | (2006.01) | |
| *C07C 2/12* | (2006.01) | |
| *C07C 7/12* | (2006.01) | |
| *B01D 15/00* | (2006.01) | |
| *B01J 20/06* | (2006.01) | |
| *C07C 2/18* | (2006.01) | |

(52) U.S. Cl.
CPC .................. *C07C 2/10* (2013.01); *B01D 15/00* (2013.01); *B01J 20/06* (2013.01); *B01J 20/08* (2013.01); *C07C 2/12* (2013.01); *C07C 2/18* (2013.01); *C07C 7/12* (2013.01); *C07C 2521/04* (2013.01); *C07C 2523/755* (2013.01); *C07C 2529/06* (2013.01); *C07C 2529/70* (2013.01)

(58) Field of Classification Search
CPC ............ C07C 7/12; C07C 11/02; C07C 11/08; C07C 11/06; C07C 2529/06; C07C 2529/70; C07C 2/10; C07C 2/12; C07C 2/18; B01J 20/08; B01J 20/06

USPC ........ 585/823, 820, 833; 208/228, 203, 229, 208/236
See application file for complete search history.

(56) References Cited

U.S. PATENT DOCUMENTS

| | | | |
|---|---|---|---|
| 4,973,790 A | 11/1990 | Beech, Jr. et al. | |
| 5,177,282 A | 1/1993 | Nierlich et al. | |
| 5,414,183 A | 5/1995 | Abrevaya et al. | |
| 5,990,372 A * | 11/1999 | Blankenship | ........ C10G 25/003 502/406 |
| 7,154,014 B1 | 12/2006 | Negiz et al. | |
| 2002/0111523 A1 | 8/2002 | Mathys et al. | |
| 2005/0137442 A1 | 6/2005 | Gajda et al. | |
| 2007/0086933 A1 | 4/2007 | Negiz et al. | |
| 2007/0213575 A1* | 9/2007 | Godsmark | ................ C07C 2/12 585/518 |
| 2008/0194903 A1* | 8/2008 | Schubert | ................ C07B 37/08 585/823 |

FOREIGN PATENT DOCUMENTS

| | | |
|---|---|---|
| WO | WO 02/060842 | 8/2002 |
| WO | WO 2004/014546 | 2/2004 |
| WO | WO 2006/089957 | 8/2006 |

OTHER PUBLICATIONS

Yang, R. T., Adsorbents: Fundamentals and Applications, Chapter 6—Silica Gel, MCM, and Activated Alumina, pp. 131-156, John Wiley & Sons, Inc. (2003).
Paglia et al., "Boehmite-Derived γ-Alumina System. 2. Consideration of Hydrogen and Surface Effects", Chemistry of Materials, vol. 16, No. 10, May 1, 2004, pp. 1914-1923, ISSN: 0897-4756, DOI: 10.1021/cm035193e.
Stepanov et al., "Interaction of Acetonitrile with Olefins and Alcohols in Zeolite H-ZSM-5: In Situ Solid-State NMR Characterization of the Reaction Products", Chem. Eur. J. 1997, vol. 3, Issue 1, pp. 47-56, ISSN: 0947-6539.
Wilson et al., "Energetics of formation of lamellar porous microstructures in γ-$Al_2O_3$", Journal of Materials Science, Springer, Netherlands, NL, vol. 15, No. 12, Jan. 1, 1980, pp. 3081-3089, ISSN: 0022-2461.
Wilson et al., "The Porosity of Aluminum Oxide Phases Derived from Well-Crystallized Boehmite: Correlated Electron Microscope, Adsorption, and Porosimetry Studies", Journal of Colloid and Interface Science, Academic Press, New York, NY, US, vol. 82, No. 2, Jan. 1, 1981, pp. 507-517, ISSN: 0021-9797.
Wilson et al., "Phase transformations and development of microstructure in boehmite-derived transition aluminas", British Ceramic Society Proceedings, Maney Publishing, GB, vol. 28, Jan. 1, 1979, pp. 281-294, XP009152719, ISSN: 0524-5141.
Yang, R. T., "Activated Alumina as special sorbents", Adsorbents Fundamentals and Applications, Wiley Intersciences, 2003, ISBN 0-471-29741-0, p. 151.
U.S. Appl. No. 14/233,199, filed Apr. 7, 2014.

* cited by examiner

*Primary Examiner* — Sharon Pregler

(57) ABSTRACT

The present invention provides an olefin oligomerization process comprising the steps of: i) reducing the level of acetonitrile in an olefin feed by contacting the feed with a non-zeolitic metal oxide; and ii) contacting the olefin feed with reduced level of acetonitrile with an olefin oligomerization catalyst under conditions suitable to oligomerize the olefin.

6 Claims, 2 Drawing Sheets

△ Example 12
☆ Example 11
□ Example 10
○ Example 9

US 9,550,705 B2

OLEFIN OLIGOMERIZATION PROCESS

CROSS REFERENCE TO RELATED APPLICATIONS

This application is a National Stage Application of International Application No. PCT/EP2012/061366, filed Jun. 14, 2012, the disclosure of which is incorporated by reference in its entirety.

FIELD OF INVENTION

The present invention relates to an olefin oligomerization process using a guard bed particularly suitable for removing acetonitrile from the olefin feed.

BACKGROUND OF THE INVENTION

The higher olefins oligomerization process converts light olefins, typically, $C_3$ to $C_6$ light olefins, to oligomers (higher olefins), typically such as octenes, nonenes and dodecenes. These higher olefins are then used in the production of various products such as plasticizers and solvents. The feedstocks used for the higher olefins oligomerization process come from various sources, such as catalytic crackers and steam crackers. Such feeds are known to contain nitrogen containing compounds, which act as poisons for the catalysts typically used in the higher olefins oligomerization process. The presence of poisons in the feeds has a significant impact on the catalyst life, and thus on the operation and economics of the higher olefins oligomerization process. It is known that acidic catalysts like solid phosphoric acid or zeolites typically used in olefin oligomerization processes are susceptible to poisoning from trace amounts of sulphur-, nitrogen- and oxygen-containing compounds in the feed. Such poisons adsorb on the acidic catalysts, blocking acid sites and pores. This causes enhanced deactivation of the catalyst and shorter catalyst life. Special precautions and feed cleanup is required in case the poison levels are too high.

At present there is no known single process that can quantitatively remove all nitrogen poisons from olefin feeds useful in the higher olefins oligomerization process to meet required feed quality specifications. Water washing sometimes can only partially removes nitriles, such as acetonitrile, from certain olefin feeds. Not only is the removal process difficult but it is expensive and generates a lot of waste water.

The interaction of acetonitrile with olefins and alcohols in zeolite H-ZSM-5 is described in Chem. Eur. J. 1997, 3, No. 1 pages 47 to 56 "Interaction of Acetonitrile with Olefins and Alcohols in Zeolite H-ZSM-5: In-Situ Solid-State NMR Characterization of the Reaction Products" Alexander G. Stepanov and Mikhail v. Luzgin.

U.S. Pat. No. 4,973,790 discloses a process for oligomerizing $C_2$ to $C_{10}$ olefins obtained by catalytic cracking of heavy crude oil. Feed pretreatment is practised to remove basic nitrogen compounds present in the light olefin feed with a water wash or guard bed. Where the pretreatment comprises at least two steps, the first step is either a water wash step or contact of feed with a solid bed having an affinity for basic nitrogen. The second step is contact with a zeolitic bed. Only use of a conventional resin guard bed is taught and exemplified. No specific nitrogen compounds are mentioned.

U.S. Pat. No. 5,414,183 discloses isomerization and etherification reactions. Nitrogen contaminants in the hydrocarbon feed stream are converted to hydrolysis products by contact with an alkaline solution. Residual products in the hydrocarbon phase may be removed by a variety of known means including water washing, stripping and adsorption.

US 2005/0137442 relates to a transalkylation process where organic nitrogen compounds, including acetonitrile and propionitrile, are removed from an aromatic feed stream by contacting the stream with an acidic molecular sieve at a temperature of at least 120° C.

US2007/0086933 discloses a transalkylation process for reacting $C_9$ aromatics with toluene to form $C_8$ aromatics such a para-xylene. The process uses an aluminium oxide guard bed prior to contacting with a translakylation catalyst in order to remove chlorides from the aromatic feed.

WO2004/014546 teaches a guard bed made of finely divided lead oxide and a particulate support material, such as aluminium oxide. This guard bed can be used to remove chlorides present in a process gas stream containing carbon monoxide and steam, before contacting with a copper containing catalyst.

SUMMARY OF THE INVENTION

The present invention provides an olefin oligomerization process comprising the steps of:
i) reducing the level of acetonitrile in an olefin feed by contacting the feed with a non-zeolitic metal oxide; and
ii) contacting the olefin feed with reduced level of acetonitrile with an olefin oligomerization catalyst under conditions suitable to oligomerize the olefins.

Preferably, the non-zeolitic metal oxide is selected from aluminum oxide, tin oxide, zirconium oxide, titanium oxide, iron oxide and tungsten oxide, more preferably, gamma aluminum oxide. In another embodiment, in step i), the feed is contacted with more than one non-zeolitic metal oxide.

Preferably, the olefin oligomerization catalyst used in step (ii) is a zeolite, nickel oxide, phosphoric acid, mixtures or combinations thereof.

In another embodiment, the non-zeolitic material used in step (i) and the oligomerization catalyst used in step ii) are in separate vessels.

The present invention also provides the use of more than one non-zeolitic metal oxide for reducing the level of acetonitrile in an olefin feed intended for use in an olefin oligomerization process.

Advantageously, one of the non-zeolitic metal oxides comprises gamma aluminium oxide.

In all the above embodiments, the olefins are preferably selected from olefins having 3 to 6 carbon atoms, preferably from 3 to 5 carbon atoms.

DETAILED DESCRIPTION

Olefin Feed

Figure 1:
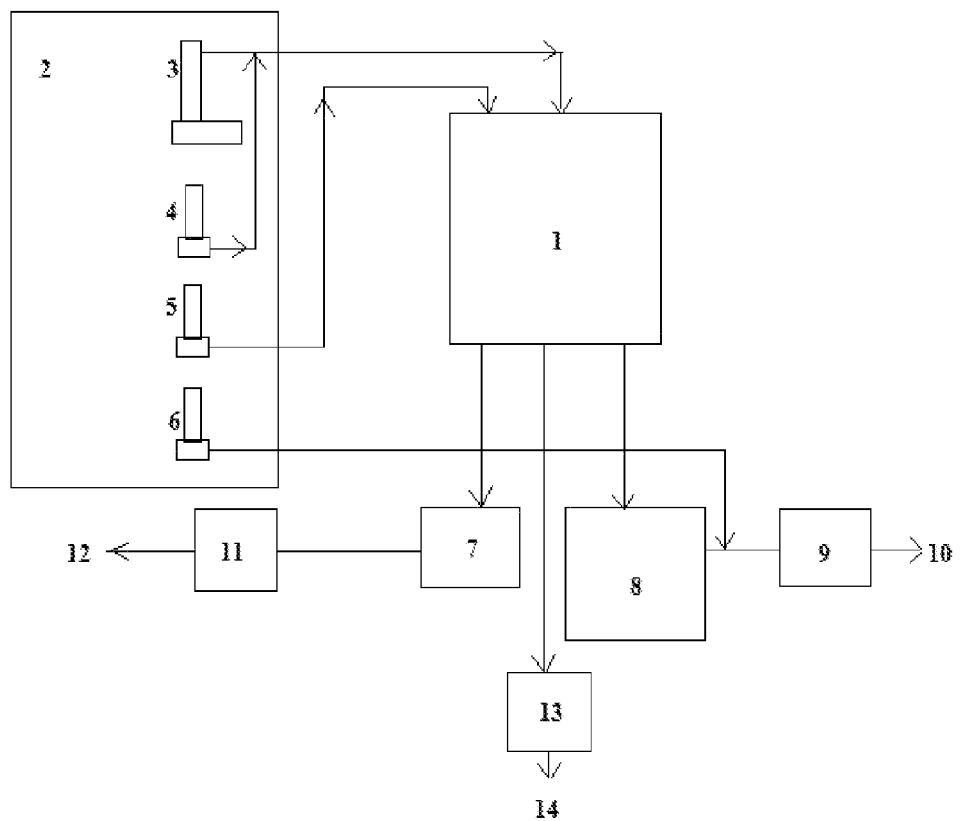
FIG. 1: provides a description of the testing equipment used in the examples.

The present invention provides a process for oligomerizing an olefin feed, which uses a step of reducing the level of acetonitrile in the olefin feed, before the olefin feed is subjected to oligomerization. As used herein, "olefins" refers to any unsaturated hydrocarbons having the formula $C_nH_{2n}$, wherein C is a carbon atom, H is a hydrogen atom, and n is the number of carbon atoms in the olefin. According to this invention, the olefins in the feed typically have from 2 to 15 carbon atoms, such as at least 3 and no more than 8 carbon atoms, and typically at least 3 and no more than 6 carbon atoms. The olefins present in the feed may also be referred to as lower olefins or light olefins.

The feed may also comprise one or more paraffins. As used herein, "paraffins" refers to any of the saturated hydrocarbons having the formula $C_nH_{2n+2}$, wherein C is a carbon atom, H is a hydrogen atom, and n is the number of carbon atoms in the paraffin. The paraffins that may be present in the olefin feed typically have from 1 to 25 carbon atoms, such as from 1 to 15 carbon atoms, and conveniently at least 3 and no more than 6 carbon atoms. Examples of suitable paraffins include methane, ethane, propane, butane, pentane, hexane, isomers thereof and mixtures thereof. If present in the feed, the paraffins may have the same or a different number of carbon atoms as the olefins.

If present, the paraffin acts as a diluent. If used, the olefin feed may comprise at least 10%, at least 25%, at least 30%, at least 35%, or at least 40% paraffin, based upon the total volume of the feed. Alternatively stated, if used, the diluent may be present in the olefin feed in the range from 10% to 40%, alternatively, from 10% to 35%, and alternatively, from 20% to 35% based upon the total volume of the feed. The diluent may also be fed to the reactor(s) separately from the olefin feed. When fed separately, the diluent may be fed in amounts equivalent to those mentioned above, where the diluent is co-fed with the feed. These amounts may not necessarily be the same as the ranges stated above given that more or less of the diluent may be necessary when fed separately to provide an equivalent.

In a class of embodiments, the olefin feed comprises olefins selected from propene, butenes, pentenes, hexenes, their isomers, and mixtures thereof. The process of this invention is especially useful for the oligomerization of feeds comprising propene, butenes, pentenes, their isomers, and mixtures thereof. As used herein, "isomers" refers to compounds having the same molecular formula but different structural formula.

Additionally, the feed may comprise an oligomer (higher olefin), for example, a dimer, such as one provided by recycling a part of an olefin oligomerization product stream. As used herein, "oligomer(s)" or "oligomer product" refers to an olefin (or a mixture of olefins) made from a few light olefins. For example, oligomers include dimers, trimers, tetramers, obtained from two, three or four light olefins of the same number of carbon atoms, mixed oligomers, obtained from 2 or more olefins having different numbers of carbon atoms and mixtures thereof. In a class of embodiments, "oligomer(s)" refers to an olefin (or a mixture of olefins) having 20 carbon atoms or less, alternatively, 15 carbon atoms or less, such as 10 carbon atoms or less, alternatively, 9 carbon atoms or less, and conveniently, 8 carbon atoms or less that has been obtained by linking two or more light olefins together. As used herein, "oligomerization process" refers to any process by which light olefins are linked together to form the oligomer(s) as defined above. As used herein, the term "oligomerization conditions" refers to any and all those variations of equipment, conditions (e.g. temperatures, pressures, weight hourly space velocities etc.), materials, and reactor schemes that are suitable to conduct the oligomerization process to produce the oligomer(s) as known and applied in the art and discussed more below.

In a class of embodiments, the feed comprises 30 wt % or more olefins, such as 40 wt % or more olefins, alternatively, 50 wt % or more olefins, alternatively, 60 wt % or more olefins, alternatively, 70 wt % or more olefins, and alternatively, 80 wt % or more olefins, based upon the total weight of the olefin feed.

In any of the embodiments described herein, the feed should be totally free, or at least substantially free, of aromatic hydrocarbon compounds that consist solely of hydrogen and carbon atoms. In this context, "substantially free" means that the olefin feed contains 25 wt % or less, preferably 15 wt % or less, more preferably 10 wt % or less, such as 5 wt % or less, and most preferably 1 wt % or less aromatic hydrocarbon, based upon the total weight of the olefin feed.

Examples of suitable olefin feeds include untreated refinery streams such as Fluidized Catalytic Cracking (FCC) streams, coke streams, pyrolysis gasoline streams or reformates.

Other examples of suitable olefin feeds include refinery feeds often referred to as Raffinate-1 (RAF-1), Raffinate-2 (RAF-2) or Raffinate-3 (RAF-3). Typically, Raffinate-1, Raffinate-2 and Raffinate-3 may be regarded as streams obtainable at various stages in the processing of crude $C_4$ streams obtained from petroleum refining processes. These streams are usually from olefin steam crackers but may also come from refinery catalytic crackers, in which case they generally contain the same components but in different proportions. The first stage of processing these crude $C_4$ refinery streams is to remove butadiene from these streams, such as by solvent extraction or hydrogenation. Butadiene is generally present in the crude $C_4$ refinery streams as 40-45 wt. % of the stream. The product obtained after butadiene removal is Raffinate-1. It generally consists of isobutylene, the two isomers of n-butene, 1-butene and 2-butene, and smaller quantities of butanes and other compounds. The next step consists in removing isobutylene, usually by reaction of isobutylene with methanol to produce methyl-tert-butylether (MTBE), which then produces Raffinate-2. Raffinate-3 (RAF-3) is less common but may be obtained after separation of 1-butene from Raffinate-2. Raffinate-3 typically has a residual 1-butene content of about 1%.

In another embodiment, the feed comprises an FCC light olefin stream that typically comprises ethane, ethylene, propane, propylene, isobutane, n-butane, butenes, pentanes, and other optional components. A specific example of such a feed is provided in Table 1.

TABLE 1

| Component | Wt. % | Mol. % |
|---|---|---|
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-Butane | 3.3 | 2.6 |
| Butenes | 22.1 | 18.3 |
| Pentenes | 0.7 | 0.4 |
| Total | 100 | 100 |

According to the present invention, any of the above-described olefin feeds contains organic nitrile contaminants, in particular, acetonitrile, which must be removed to an acceptable level before the olefins undergo oligomerization. Typically, the nitrile content in the olefin feed upstream of the guard bed may be about 3 ppm or more, such as about 5 ppm or more, typically, 10 ppm or more, such as 20 ppm or more, and yet alternatively, 30 ppm or more, calculated on a nitrogen atom basis by weight (wt ppm), with respect to the total weight of hydrocarbon in the olefin stream.

Optionally, the olefin feed may also be hydrated (i.e., contacted with water) prior to oligomerization. In an embodiment, sufficient water is used to saturate the feed. In particular, the feed may comprise from about 0.01 to about 0.25, alternatively, from about 0.02 to about 0.20, and alternatively, from about 0.03 to about 0.10, mol % water based on the total hydrocarbon content of the feed. If desired and by way of example, the water content of the feed may be increased by passage through a thermostatted water saturator. The olefin feed used in the oligomerization step can therefore be wet or dry.

Guard Bed and Acetonitrile Removal Process

The present invention provides a process for oligomerizing an olefin feed, which uses a step of reducing the level of acetonitrile in the olefin feed, before the olefin feed is subjected to oligomerization. This step of reducing the level of acetonitrile in the olefin feed is accomplished by containing the olefin feed with a non-zeolitic metal oxide. Contacting is typically done by flowing the olefin feed through a bed of the non-zeolitic metal oxide, thereby allowing acetonitrile to be adsorbed on the non-zeolitic metal oxide. Such a bed of non-zeolitic metal oxide therefore acts as a guard bed, that is, it reduces the level of acetonitrile present in the olefin to levels where acetonitrile will no longer interfere in the subsequent olefin oligomerization step. At the same time, the guard bed avoids oligomerization or any other reactions which might compete with the guard bed's role of adsorbing acetonitrile (ACN) from the olefin feed.

The guard bed comprises a non-zeolitic metal oxide, selected from aluminum oxide (also referred to as alumina), tin oxide, zirconium oxide, titanium oxide, iron oxide, magnesium and tungsten oxide, silicon oxide, copper oxide, nickel oxide, zinc oxide, and mixtures thereof. Preferably the guard bed metal oxide comprises alumina. Alumina crystallizes in different forms, which have different structures and compositions. Of these, the most preferred form is gamma-alumina obtainable from boehmite. The present inventors have realized that gamma-alumina, when employed in a non-zeolitic guard bed, is most effective at adsorbing acetonitrile from a contaminated olefin feed intended for use in an olefin oligomerization process.

The guard bed can comprise two or more of the metal oxides listed above and in any combination. There are different ways to prepare the multi metal oxide compositions, including physical mixing and co-precipitation methods. The metal oxide or multi metal oxide used in the guard bed may also contain metals and noble metals added to the metal oxide or multi metal oxide by impregnation or other preparation methods.

It is preferred that gamma-alumina is one of the metal oxides where the guard bed comprises more than one metal oxide. It is most preferred that the multi metal oxide used as guard bed comprises gamma-alumina and iron oxide.

The olefin feed can be contacted with the guard bed at temperatures from about 50° C. to about 350° C., preferably from about 50° C. to 320° C. In one embodiment, the preferred temperature range is from about 100° C. to about 300° C., alternatively, from about 150° C. to about 250° C., and alternatively, from about 200° C. to about 250° C. However, if the step of removing acetonitrile from the olefin feed is carried out in a reaction vessel that is separate from the oligomerization reactor, lower temperatures can prove suitable too, such as from about 50° C. to below about 100° C., such as from about 50° C. to about 95° C.

The pressure may be in the range of from about 400 psig to about 4000 psig (2860 kPa to 27688 kPa), and preferably, from about 500 psig to about 1500 psig (3550 kPa to 10446 kPa). The olefin weight hourly space velocity may be in the range of from about 0.1 hr$^{-1}$ to about 20 hr$^{-1}$ or from about 0.5 hr$^{-1}$ to about 5 hr$^{-1}$. In one embodiment, the process is conducted at a temperature of 80-350° C., an olefin weight hourly space velocity of 0.1-20 hr$^{-1}$, and a pressure of 2860-27688 kPa. In another embodiment, the process is conducted at a temperature of 130-320° C., an olefin weight hourly space velocity of 0.5-5 hr$^{-1}$ and a pressure of 3550-10446 kPa.

The non-zeolite metal oxide used as guard bed can be placed in the same vessel as the vessel in which olefin oligomerization takes place or it can be in separate vessels. Whether in the same or different vessels the non-zeolitic metal oxide used as guard bed is placed upstream of the olefin oligomerization catalyst. The benefit of the olefin oligomerization catalyst and guard bed being in separate vessels is that there can be independent control of process conditions such as temperature and pressure to ensure optimal rates for both steps. The benefit of the catalyst and guard bed being in the same vessel is that the arrangement for the oligomerization process is more compact and easier to construct. More than one guard bed having the same or different composition can be used. The presence of more than one guard bed enables a longer run length. Also, while one or more guard beds are in use, the other(s) can be regenerated. This ensures a continuous process for the removal of acetonitrile and purification of the olefin feed.

After contacting with the non-zeolitic metal oxide or multi metal oxides in the guard bed, the nitrile content in the olefin stream downstream of the guard bed is about 1.50 ppm or less, alternatively, 1.00 ppm or less, such as 0.50 ppm or less, alternatively, 0.30 ppm or less, 0.20 ppm or less, and yet preferably 0.10 ppm or less calculated on a nitrogen atomic basis by weight (wt ppm) relative to the total weight of hydrocarbons in the olefin stream.

Oligomerization

Once the level of acetonitrile in the feed has been decreased to suitable levels, the olefin feed is contacted with a catalyst under conditions suitable to form higher olefins through oligomerization.

One or more catalysts may be used for the oligomerization. Any catalyst suitable for olefin oligomerization, whether homogeneous or heterogeneous, may be used. Heterogeneous catalysts may be crystalline or amorphous (non-crystalline) catalysts. Crystalline catalysts include without limitation molecular sieve catalysts such as, for example, zeolite catalysts, in particular, H-zeolites (i.e. zeolites in their proton or acidic form).

Non-crystalline heterogeneous catalysts include without limitation solid acid catalysts such as, for example, solid phosphoric acid (SPA) catalysts and supported metal catalysts or supported metal oxide catalysts. Non-limiting examples of olefin oligomerization processes using such catalysts may be found as follows. Olefin oligomerization using SPA catalysts is disclosed for example in U.S. Pat. No. 6,025,533, WO 92/13818 or WO 2005/058777. The CATPOLY™ Process (UOP and Sud Chemie) employs phosphoric acid on a silica support. The OCTOL™ Process (UOP/Huels (now Evonik)) employs a nickel containing catalyst on a silica/aluminium oxide support. See Make plasticizer olefins via n-butene dimerization R. H, Friedlander et al., Hydrocarbon Processing, February 1986, pages 31-33, and U.S. Pat. No. 5,177,282. Amorphous silica aluminium oxide supports are useful and commonly utilized. Solid acid catalysts may be optionally practiced with promoters such as $TaF_5$.

In another embodiment, olefin oligomerization can take place in the presence of a homogenous catalyst. Non-limiting examples of such catalysts are provided as follows. The IFP (now Axens) DIMERSOL® processes employs a Ni-based homogeneous catalyst. (Y. Chauvin et al. Chemistry and Industry, 1974, 373-378). U.S. Pat. No. 4,225,743 discloses a homogeneous catalyst system suitable for olefin oligomerization, consisting of a Nickel (II) salt of octanoic acid, ethylaluminium dichloride, and a free fatty acid. Preferably, the catalyst is selected from catalysts comprising a zeolite, nickel oxide or phosphoric acid.

The term "zeolite" is often used to describe the aluminosilicate members of the family of microporous solids known as "molecular sieves". The term molecular sieve refers to a particular property of these materials, i.e., the ability to selectively sort molecules based primarily on a size exclusion process. This is due to a very regular pore structure of molecular dimensions. The maximum size of the molecular or ionic species that can enter the pores of a zeolite is controlled by the dimensions of the channels. These are conventionally defined by the ring size of the aperture, where, for example, the term "8-ring" refers to a closed loop that is built from 8 tetrahedrally coordinated silicon or aluminum atoms and 8 oxygen atoms. These rings are not always perfectly symmetrical due to a variety of effects, including strain induced by the bonding between units that are needed to produce the overall structure, or coordination of some of the oxygen atoms of the rings to cations within the structure. Therefore, the pores in many zeolites may not be cylindrical.

In an embodiment, the at least one zeolite catalyst may include a medium pore size molecular sieve having a Constraint Index of about 1 to about 12. Constraint Index and a method of its determination are described in, for example, U.S. Pat. No. 4,016,218.

Examples of the at least one zeolite catalyst include those of the TON framework type (for example, ZSM-22, ISI-1, Theta-1, Nu-10, and KZ-2), those of the MTT framework type (for example, ZSM-23 and KZ-1), those of the MFI framework type (for example, ZSM-5), those of the MFS framework type (for example, ZSM-57), those of the MEL framework type (for example, ZSM-11), those of the MTW framework type (for example, ZSM-12), those of the EUO framework type (for example, EU-1), those of the AEL framework type (for example, SAPO-11), members of the ferrierite family (for example, ZSM-35) and members of the ZSM-48 family of molecular sieves (for example, ZSM-48). Other examples include zeolites of the MWW family (e.g., MCM-22, MCM-48), zeolites of the MOR framework type, or zeolite beta. As used herein, the term "framework type" is used as described in the Atlas of Zeolite Framework Types, Ch. Baerlocher, L. B. McCuster and D. H. Ohlson, Elsevier 2007.

Preferably, the zeolite is selected from at least one of ZSM-5, ZSM-11, ZSM-12, ZSM-18, ZSM-22, ZSM-23, ZSM-35, ZSM-38, ZSM-48, ZSM-50, zeolites of the MFS framework type, for example ZSM-57, zeolites having the TON framework type, for example ZSM-22, and mixtures thereof.

Mixtures of two or more of zeolites may be used in the oligomerization process. For example, the mixture may include ZSM-22 and ZSM-57 or ZSM-22 and ZSM-5 or ZSM-57 and ZSM-5. The at least one zeolite catalyst may also be combined with other types of catalysts such as a solid phosphoric acid (sPA) catalyst, nickel oxide.

The zeolite used in the oligomerization catalyst may have an average crystallite or particle size of up to 15 µm, such as within the range of from 0.01 to 6 µm, alternatively, from 0.05 to 5 µm, and alternatively, from 0.1 to 3 µm. As used herein, "average particle size" refers to the arithmetic average of the diameter distribution of the crystals on a volume basis.

Preferably, the zeolite is used in its proton, or acidic form. To obtain this form, an as-synthesized molecular sieve that has been obtained in an alkaline or alkaline-metal form is advantageously converted to its acid form, for example, by acid treatment, e.g., by HCl, acetic acid, etc. or by ion exchange, for example, ammonium ion exchange. Subsequently, it may undergo calcination before use. The calcined materials may be post-treated, such as by steaming.

The at least one zeolite catalyst may be produced by any suitable method known for the given type of zeolite. One technique includes heating a reaction mixture containing a source of silicon oxide, a source of aluminum oxide and, if appropriate, an organic promoter, for example, a nitrogen or phosphorus-containing organic base, together optionally, with an alkali metal base, and separating the porous aluminosilicate crystals (zeolite precursor crystals) formed. The precursor crystals are then calcined in air or oxygen at a temperature exceeding or about 500° C., for example, at a temperature of 550° C. for about 10 to about 20 hours. As recognized in the art, calcination temperatures and durations may vary depending on the type of zeolite catalyst or combination of zeolite catalysts selected. In one embodiment, the calcined material is exchanged with ammonium ions ($NH_4+$) and subjected to conditions under which the ammonium ions decompose, with the formation of ammonia and a proton, thus, producing an acidic form of the at least one zeolite catalyst. Alternatively, the acidic form of the catalyst may be obtained by acid exchange with hydrochloric acid, acetic acid, etc. If desired, however, the calcined material may be used as a catalyst without first being exchanged with ammonium ions, since the material already possesses acidic sites.

Ammonium exchanged and calcined mono-dimensional 10-rings zeolites (e.g., ZSM-22 and ZSM-23) may be treated to selectivate their surface, thereby, forming a selectivated catalyst. This selectivation may be achieved in numerous ways. In an embodiment, the at least one zeolite catalyst may be titrated with an organic nitrogen base, such as collidine. See, for example, U.S. Pat. No. 5,026,933. Another example is by depositing a crystalline Si:Al layer on a core of zeolite where this layer has a higher Si:Al ratio than the untreated zeolite. See, for example, U.S. Pat. No. 6,013,851.

Although much of the discussion above is directed to aluminosilicate zeolites, it is possible to use material in which silicon and aluminum have been replaced in whole or in part by other elements, for example, any one or more of a Group 2 to Group 15 atom. For example, silicon may be replaced by or contacted with germanium and aluminum or may be replaced with boron, gallium, chromium, and iron. As used herein, these materials containing such replacement lattice elements may also be termed zeolites.

It may be desirable to incorporate the molecular sieves or zeolites mentioned above with another material that is resistant to the temperatures and other conditions employed in the olefin oligomerization process. Thus the molecular sieves or zeolites may be used in the form of an extrudate with binder, where the molecular sieve or zeolite is dispersed within a conventional binder. Binding is typically done by forming a pill, sphere, or extrudate. The extrudate is usually formed by extruding the molecular sieve, optionally in the presence of a binder, and drying and calcining the resulting extrudate. The binder materials used are resistant to the temperatures and other conditions, e.g., mechanical attrition, which occur in various hydrocarbon conversion processes.

Examples of binder materials that may be employed with the molecular sieves or zeolties suitable for use in the process of the invention include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Naturally occurring clays which may be used include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or after being subjected to calcination, acid treatment or chemical modification. Examples of other materials include porous matrix materials such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Exemplary catalyst materials and processes for making such catalysts may also be found in U.S. Pat. Nos. 3,960,978, 4,016,218, 4,021,502, 4,381,255, 4,560,536, 4,919,896, 5,446,222, 5,672,800, 6,143,942, 6,517,807, 6,884,914, U.S. Patent Application Publication No. 2006/0199987, EP 746 538 A, WO 1994/12452 WO 2005/118512, WO 2005/118513, WO 2007/006398, and WO 2008/088452.

According to the present invention, the olefin feed with reduced level of acetonitrile is contacted with a catalyst under conditions suitable to oligomerize the olefins. The olefin oligomerization reaction system may include one or more of a fixed bed reactor, a packed bed reactor, a tubular reactor, a fluidized bed reactor, a slurry reactor, a continuous catalyst regeneration reactor, and any combination thereof. These reactors may be operated in any combination such as, for example, in series and/or parallel sequence. In several embodiments, they may be operated in semi-continuous (i.e., continuous but down for routine maintenance), continuous, or batch mode.

The oligomerization conditions may temperatures from about 80° C. to about 350° C. Close to and above the upper end of the range, deoligomerization rates increase and may predominate over the oligomerization reaction providing an upper limit to practical operation. More typically, the reaction temperature is from about 130° C. to about 320° C., preferably from about 135° C. to about 310° C., and even more preferably from about 160° C. to about 270° C.

The pressure may be in the range of from about 400 psig to about 4000 psig (2860 kPa to 27688 kPa), and alternatively, from about 500 psig to about 1500 psig (3550 kPa to 10446 kPa). The olefin weight hourly space velocity based on catalyst, may be in the range of from about 0.1 hr$^{-1}$ to about 20 hr$^{-1}$ or from about 0.5 hr$^{-1}$ to about 5 hr$^{-1}$. In one embodiment, process is conducted at a temperature of 80-350° C.; an olefin weight hourly space velocity of 0.1-20 hr$^{-1}$; and a pressure of 2860-27688 kPa. In another embodiment, the process is conducted at a temperature of 130-320° C.; an olefin weight hourly space velocity of 0.5-5 hr$^{-1}$; and a pressure of 3550-10446 kPa.

In a class of embodiments, the oligomers formed in the olefin oligomerization step of the process of the invention may include a hydrocarbon composition comprising at least 80 wt %, alternatively, at least 90 wt % based upon the total weight of the reactor effluent (the final reactor effluent if one or more reactors are utilized) of $C_6$ to $C_{20+}$ olefin or a mixture thereof.

The oligomer (higher olefin) product is useful in many applications and is the starting material for further conversion processes. For example, the oligomer product may be polymerized to produce polyolefins that have application in the plastic industry or polymerized to form synthetic basestocks for lubricants. The oligomer product may undergo hydroformylation and subsequently hydrogenation to produce alcohols. The alcohols may be used in industry such as, for example, solvents, or be incorporated into the production of detergents/surfactants. The alcohols may further be used in many other areas of industry such as, for example, undergoing esterification to produce esters that have application as plasticizers. The oligomer product may also be a blend component for fuels.

The present invention will now be illustrated by way of the following non-limiting examples.

EXAMPLES

Olefin Feeds

In these examples, the following olefin feeds were used:
Propylene feed: containing 50% propylene, 40% propane and 10% butane, by weight.
Butene/pentene feed containing 35% 1-butene, 25% 1-pentene, 30% butane, 10% propane.
The olefin feeds were spiked with acetonitrile (ACN) or ACN and dimethyldisulfide (DMDS). To some feeds, water was added to make feeds containing 300 ppm of dissolved water in the hydrocarbon phase.

Non-Zeolitic Metal Oxides Used as Guard Beds

The non-zeolitic metal oxides used as guard beds were prepared by the following method.
a) Pure Metal Oxides and Physical Mixtures of Metal Oxides.
The amounts of metal oxides mentioned in Table 2 below were mixed at room temperature with 30 to 40 ml of deionized (DI) water in a blender cup. The mixture was stirred for about 4 hours at room temperature to form a uniform slurry. The resultant slurry was then centrifuged to remove the supernatant without additional washing. The obtained solid was dried overnight at 80° C. in air and calcined at 540° C. for 4 hours in air, then ground to make a uniform powder. The powder was then pressed and sized before loading in the reactor.

TABLE 2

| Ref. | Starting Material | Amount used (g) | Calcined product |
|---|---|---|---|
| A | Pseudoboehmite * | 2.78 g * | γ-alumina |
| B | Iron (III) oxide | 2.0 g | $Fe_2O_3$ |
| C | Tungsten oxide | 2.0 g | $WO_3$ |
| D | Tin oxide | 2.0 g | $SnO_2$ |
| E | Titanium oxide | 2.0 g | $TiO_2$ |
| F | Zirconium oxide | 2.0 g | $ZrO_2$ |
| G | Pseudoboehmite * | 2.78 g * | γ-alumina/ |
|   | Iron (III) oxide | 2.0 g | $Fe_2O_3$ phys. mix |

TABLE 2-continued

| Ref. | Starting Material | Amount used (g) | Calcined product |
|------|-------------------|-----------------|------------------|
| H | Pseudoboehmite *<br>Tungsten oxide | 2.78 g *<br>2.0 g | γ-alumina/<br>WO phys. mix |
| I | Cab-osil **<br>Iron (III) oxide | 2.06 g **<br>2.0 g * | $SiO_2/Fe_2O_3$<br>phys. mix |

* Pseudoboehmite available from UOP having 72% alumina: 2.78 g corresponds to 2 g alumina.
** Cabosil available from Cobalt Corporation, >97% silica and 200 m²/g.

b) Co-Precipitated Mixed Metal Oxides (Ref. J—$Fe_2O_3$/$Al_2O_3$ Ppt).

A solution of $Fe(NO_3)_3$ (12.52 ml of 1.0 M solution, corresponding to 1.0 g of $Fe_2O_3$) was mixed with a solution of $Al(NO_3)_3$ (19.62 ml of 1.0 M solution, corresponding to 1.0 g $Al_2O_3$) in a beaker with a big stirrer bar, followed by adding 70 ml of DI water for diluting the above-mentioned solution. A 10 wt. % ammonium hydroxide solution was added drop wise with stirring until reaching a neutral pH (pH of 7 to 8), and thereby forming a gel-like slurry. The resulting slurry was continuously stirred for another 4 hours at room temperature, recovered by centrifugation, dried overnight at 80° C. and finally calcined at 540° C. in air for 4 hours. The obtained solids were ground pressed and sized before loading in the reactor.

Olefin Oligomerization Catalyst

The catalyst used was based on a ZSM-57 with $Si/Al_2$ ratio of 45 made according to U.S. Pat. No. 7,011,810 B2. The zeolite was combined with an alumina binder to form an extrudate containing 50% of the zeolite. The extrudates were crushed and sieved to a mesh size of 0.3 to 0.6 mm before loading in the reactor.

General Testing Procedure

All experiments were carried out in small reactor tubes of a Parallel Fixed Bed Reactor (PFBR), which contains 16 thin wall (0.5 mm) metal (stainless steel SS 316) reactor tubes. Each tube used for testing was filed with 170 mg of oligomerization catalyst, on top of which a non-zeolitic metal oxide material was added as a guard bed in amounts varying from 0 to 160 mg. The tubes were operated in downflow mode, so the non-zeolitic metal oxide was located upstream of the oligomerization catalyst. The PFBR was operated at a constant set point temperature of 220° C. (examples 1-28) or 240° C. (examples 29-31), at a pressure of 1000 psig (6998 kPa) and feed weight hourly space velocity (WHSV) of 20 hr$^{-1}$ based on catalyst. The total reactor effluent was analyzed by Gas Chromatography (Agilent GC) to measure conversion, selectivity and isomer distribution.

Further details regarding the PFBR are provided below, with reference to FIG. 1.

The PFBR reactor (1) was pressurized with nitrogen using back pressure controllers (BPCs) (Bell Jar BPC (7), Heated BPC (8) and Heated Needle Valve BPC (9)) to 1000 psig (6998 kPa). Reactor $N_2$ Mass Flow Controller (MFC) (4) and Bell Jar $N_2$ MFC (5) located in a Reactor Feed Assembly unit (2) were used to pressurize the reactor and the bell jar (11), respectively. The bell jar (11) and the PFBR reactor (1) were simultaneously pressurized to maintain a differential pressure between the PFBR reactor (1) and the bell jar (11) of less than 50 psig (345 kPa) at all times, to ensure that the O-rings and pressure fittings inside the bell jar (11) sealed against a small (50 psig) (345 kPa) pressure drop even though the reactor pressure was much high (1000 psig) (6998 kPa). The reactor was heated to the reaction temperature, and all heated transfer lines, BPCs (except the Bell Jar BPC (7)), and GC inlet valve box located in GC unit (9) were controlled at 200° C. Once the reactor was at reaction temperature, the reactor feed was switched from nitrogen (Reactor $N_2$ MFC (4) was closed) to premixed liquid feed to flow reactants at a predetermined weight hourly space velocity (WHSV) using dual head continuous flow Isco pumps (3) located in Reactor Feed Assembly unit (2). The liquid feed flowed through a microfluidic flow splitter (not shown) to distribute flow equally into the 16 PFBR reactor tubes containing the catalyst with or without guard bed metal oxide. The flow splitter temperature was maintained at 150° C. to preheat the liquid feed before it entered the reactor tube. Thin wall (0.5 mm) metal (SS 316) tubes (ID~4 mm) were used to ensure good heat transfer between the reactor heat spreader (copper block with through holes for reactor tubes) and reactor tubes. Dilution nitrogen was added using Dilution $N_2$ MFC (6) just after Heated Needle Valve BPC (8) to keep the product dew point below 200° C. and to prevent condensation of high boiling products and for gas-phase injection of products into GC unit (9) for analysis before collection into a waste unit (10). The product not collected from the reactor for GC analysis was directed to Heated BPC (9) before being sent into a waste unit (10).

Product Analysis

A dual injection GC method was used to analyze the product. In this dual injection method, a first column (HP-1 column fitted with a front split inlet with hydrogenation catalyst) was used with a front FID detector to determine selectivity and a second column (QPLOT column) was used with a back FID to analyze the $C_3$ to $C_5$ component of the product for conversion and subsequently, the catalyst life.

Figure 2:
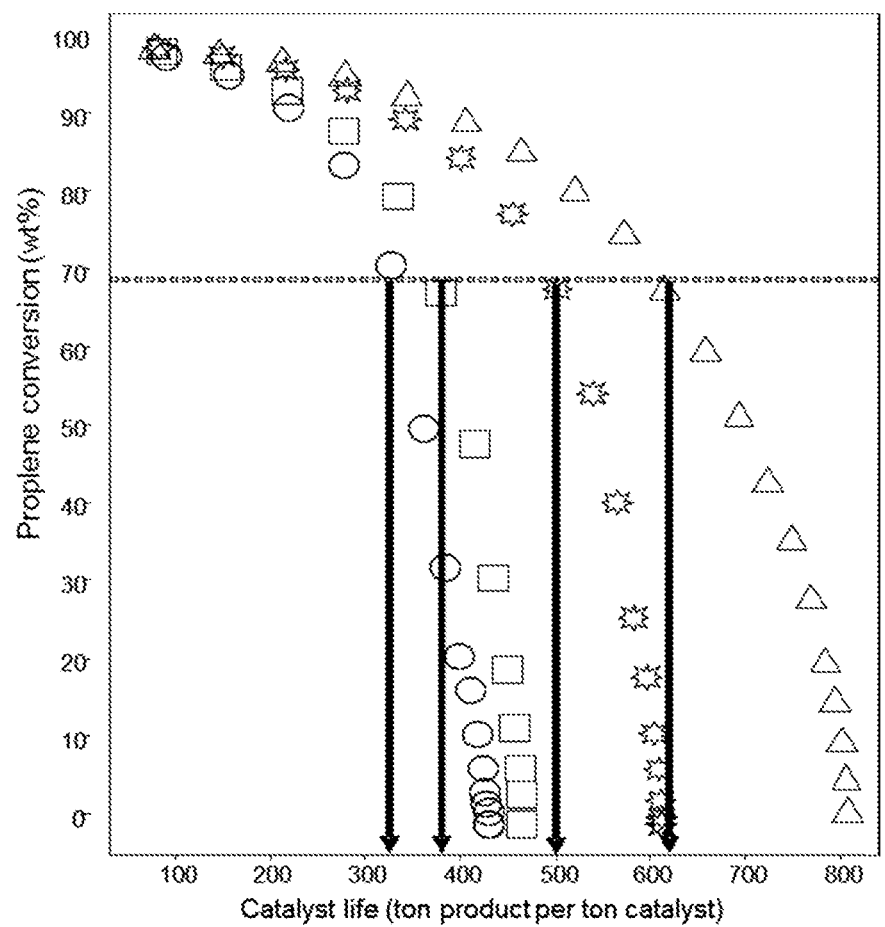
FIG. 2: provides the results obtained with different guard bed materials.

As used herein, catalyst life or "cat life" (Tpdt/Tcat or t/t) describes the number of tons of product produced per ton of formulated catalyst, at a set point temperature, at a given space velocity and until a given olefin conversion rate is reached. The method to determine catalyst life is illustrated in FIG. 2, with respect of Examples 9-12 described in further detail below.

Examples 1-16

Tests with Propylene Feed Containing 1 wt ppm ACN

In these examples, the general testing procedure described above was used. The PFBR was operated at a constant set point temperature of 220° C., a pressure of 1000 psig (6998 kPa) and an olefin weight hourly space velocity (WHSV) of 20 hr$^{-1}$ based on catalyst. The catalyst life was determined as point when the catalyst has reached 70% olefin conversion under these fixed conditions. The results are summarized in Table 3.

TABLE 3

| Ex. | Guard bed type (Ref.) | Amount of metal oxide in guard bed (mg) | Cat. Life (70% conversion) |
|-----|----------------------|------------------------------------------|----------------------------|
| 1 | None | 0 | 269 |
| 2 | γ-alumina (A) | 80 | 648 |
| 3 | None | 0 | 294 |

TABLE 3-continued

| Ex. | Guard bed type (Ref.) | Amount of metal oxide in guard bed (mg) | Cat. Life (70% conversion) |
|---|---|---|---|
| 4 | γ-alumina (A)* | 80 | 589 |
| 5 | α-alumina | 80 | 329 |
| 6 | SiO$_2$ | 80 | 334 |
| 7 | TiO$_2$ (E) | 80 | 500 |
| 8 | ZrO$_2$ (F) | 80 | 468 |
| 9 | γ-alumina (A) | 10 | 334 |
| 10 | γ-alumina (A) | 20 | 379 |
| 11 | γ-alumina (A) | 40 | 500 |
| 12 | γ-alumina (A) | 80 | 620 |
| 13 | γ-alumina/Fe$_2$O$_3$ phys. mix (G) | 40 | 470 |
| 14 | γ-alumina/Fe$_2$O$_3$ phys. mix (G) | 80 | 709 |
| 15 | Fe$_2$O$_3$/Al$_2$O$_3$ ppt (J) | 40 | 570 |
| 16 | SiO$_2$/Fe$_2$O$_3$ phys. mix (I) | 80 | 304 |

*γ-alumina purchased from UOP

Example 1 gives the reference catalyst life (cat life) for the oligomerization catalyst without a guard bed.

Example 2 shows a large cat life improvement when applying 80 mg of gamma aluminium oxide guard bed material inside the reactor on top of the olefin oligomerization catalyst.

For example 3 no guard bed was put on top of the oligomerization catalyst inside the reactor, but instead 1.3 g of Al$_2$O$_3$ was used as guard bed in a separate reactor at room temperature in series in front of the reactor with the oligomerization catalyst. Example 3 shows no effect of a pretreatment using 1.3 g of the Al$_2$O$_3$ guard bed placed in a separate reactor at room temperature.

Example 5 shows that alpha-alumina was not as good as gamma-alumina as a guard bed material.

Comparing example 2 and 4 (aluminium oxide guard beds prepared from pseudoboehmite and ready-made gamma aluminium oxide, respectively) with examples 6, 7 and 8 (SiO$_2$, TiO$_2$ and ZrO$_2$) shows that the aluminium oxide used in example 2 and 4 are more effective guard beds than the SiO$_2$, TiO$_2$ and ZrO$_2$ used in these experiments.

Examples 9 to 12 are with different amounts of γ-alumina and show that with more guard bed material, the catalyst life is longer. The method sued to determine the catalyst life is determined is illustrated in FIG. 2 for these examples.

Examples 13 to 15 show the effect of 50/50 wt % Fe$_2$O$_3$/Al$_2$O$_3$ guard bed types (physical mix or precipitated). These results show that mixed oxides are very efficient as well for removing acetonitrile from olefin feeds.

Examples 17-23

Tests with Propylene Feed Containing 1 wt ppm ACN and 300 wt ppm H$_2$O

In these examples, the general testing procedure was used. The PFBR was operated at a constant set point temperature of 220° C., a pressure of 1000 psig (6998 kPa) and feed weight hourly space velocity (WHSV) of 20 hr$^{-1}$ based on catalyst. The catalyst life was determined as point when the catalyst has reached 70% olefin conversion under these fixed conditions. The results are summarized in Table 4.

TABLE 4

| Ex. | Guard bed type (Ref.) | Amount of metal oxide in guard bed (mg) | Cat. Life (70% conversion) |
|---|---|---|---|
| 17 | None | 0 | 133 |
| 18 | γ-alumina (A) | 20 | 205 |
| 19 | γ-alumina (A) | 40 | 296 |
| 20 | γ-alumina (A) | 80 | 590 |
| 21 | γ-alumina (A) | 160 | 821 |
| 22 | γ-alumina/Fe$_2$O$_3$ phys. mix (G) | 80 | 653 |
| 23 | Fe$_2$O$_3$/Al$_2$O$_3$ ppt (J) | 80 | 587 |

Example 17 shows a cat life at 70% conversion of 133 t/t (ton product per ton catalyst). This is lower than the 269 t/t (example 1) on dry feed with 1 wt ppm ACN indicating an additional poisoning effect of the dissolved water. When having a certain amount of Al$_2$O$_3$ guard bed (examples 18 to 21) inside the reactor and heated to 220° C., the cat life can be improved significantly and the effect is more pronounced with more guard bed material present.

These results also illustrates that the guard bed is still effective on wet feed. Comparing the same amount of guard bed and same guard bed type on dry and wet feed (example 12 vs example 20) shows a longer catalyst life on dry feed compared to wet feed.

Examples 24-28

Tests with Propylene Feed Containing 1 wt ppm ACN, 1 wt ppm DMDS and 300 wt ppm H$_2$O In these examples, the general testing procedure was used. The PFBR was operated at a constant set point temperature of 220° C., a pressure of 1000 psig (6998 kPa) and feed weight hourly space velocity (WHSV) of 20 hr$^{-1}$ based on catalyst. The catalyst life was determined as point when the catalyst has reached 70% olefin conversion under these fixed conditions. The results are summarized in Table 5.

TABLE 5

| Ex. | Guard bed type (Ref.) | Amount of metal oxide in guard bed (mg) | Cat. Life (70% conversion) |
|---|---|---|---|
| 24 | None | 0 | 113 |
| 25 | γ-alumina (A) | 80 | 238 |
| 26 | γ-alumina/Fe$_2$O$_3$ phys. mix (G) | 40 | 216 |
| 27 | γ-alumina/Fe$_2$O$_3$ phys. mix (G) | 80 | 380 |
| 28 | Fe$_2$O$_3$/Al$_2$O$_3$ ppt (J) | 80 | 375 |

When compared to Example 17, Example 24 shows that DMDS further lowers the catalyst life.

Examples 25 to 28 show that γ-alumina and 50/50 wt % Fe$_2$O$_3$/Al$_2$O$_3$ improve the catalyst life even when DMDS is present in the olefin feed.

Examples 29-31

Tests with Butene/Pentene Feed without any Contaminant or with 1 wt ppm ACN and 1 wt ppm DMDS In these examples, the general testing procedure was used. The PFBR was operated at a constant set point temperature of 240° C., a pressure of 1000 psig (6998 kPa) and feed weight hourly space velocity (WHSV) of 20 hr$^{-1}$ based on catalyst. The catalyst life was determined as point when the catalyst has reached 70% total olefin conversion under these fixed conditions. The results are summarized in Table 6.

TABLE 6

| Ex. | Feed type | Guard bed type (Ref.)/ | Amount of metal oxide in guard bed (mg) | Cat. Life (70% conversion) |
|---|---|---|---|---|
| 29 | No contaminants | None | 0 | 680 |
| 30 | 1 ppm ACN; 1 ppm DMDS | None | 0 | 320 |
| 31 | 1 ppm ACN; 1 ppm DMDS | γ-alumina (A) | 80 | 520 |

Examples 29 and 30 show that the presence of ACN and DMDS in the butene/pentene feed significantly reduces the catalyst. When placing an aluminium oxide guard bed (80 mg) in the reactor on top of the catalyst, the catalyst life is greatly improved (example 31).

The invention claimed is:

1. An olefin oligomerization process comprising the steps of:
   i) reducing a level of acetonitrile and dimethyldisulfide in an olefin feed by contacting the feed with a non-zeolitic material consisting of a gamma alumina oxide and an iron oxide; and
   ii) contacting the olefin feed having a reduced level of acetonitrile and dimethyldisulfide with an olefin oligomerization catalyst under conditions suitable to oligomerize the olefins.

2. The process according to claim 1, wherein the olefin oligomerization catalyst used in step (ii) is selected from the group consisting of a zeolite, nickel oxide, phosphoric acid, and mixtures thereof.

3. The process according to claim 1, wherein the non-zeolitic material used in step (i) and the olefin oligomerization catalyst used in step (ii) are in separate vessels.

4. The process according to claim 1, wherein the temperature employed during step i) is in the range of 150 to 250° C.

5. The process according to claim 1, wherein the olefin is selected from olefins having 3 to 6 carbon atoms.

6. The process according to claim 1, wherein the gamma alumina oxide and the iron oxide are a physical mixture.

* * * * *

UNITED STATES PATENT AND TRADEMARK OFFICE
CERTIFICATE OF CORRECTION

PATENT NO. : 9,550,705 B2
APPLICATION NO. : 14/233199
DATED : January 24, 2017
INVENTOR(S) : Geraldine Tosin et al.

Page 1 of 1

It is certified that error appears in the above-identified patent and that said Letters Patent is hereby corrected as shown below:

On the Title Page

At Item (73), delete "Assignee: ExxonMobill Chemical Patents Inc.", and substitute therefore: "Assignee: ExxonMobil Chemical Patents Inc."

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*